United States Patent [19]

Karrer

[11] Patent Number: 4,556,714
[45] Date of Patent: Dec. 3, 1985

[54] N-(POLYALKYLPIPERIDINYL)-CARBAMATES OF POLYOLS

[75] Inventor: Friedrich Karrer, Zofingen, Switzerland

[73] Assignee: Ciba-Geigy Corporation, Ardsley, N.Y.

[21] Appl. No.: 571,060

[22] Filed: Jan. 16, 1984

[30] Foreign Application Priority Data

Jan. 24, 1983 [CH] Switzerland .............. 383/83

[51] Int. Cl.$^4$ ............... C07D 211/34; C07D 211/58
[52] U.S. Cl. .................... 546/190; 546/187; 546/189; 544/130; 544/364
[58] Field of Search ........ 546/189, 190, 187; 544/130, 364

[56] References Cited

U.S. PATENT DOCUMENTS

| 2,527,240 | 7/1947 | Baird et al. ............... 546/189 |
| 3,684,765 | 8/1972 | Matsui et al. ............. 546/189 |
| 3,904,581 | 9/1975 | Murayama et al. ........ 524/99 |
| 3,937,711 | 2/1976 | Cook ........................... 524/99 |
| 4,191,683 | 3/1980 | Brunetti et al. ............ 524/102 |
| 4,233,412 | 11/1980 | Rody et al. .................. 525/167 |
| 4,348,524 | 9/1982 | Karrer et al. ................ 546/190 |
| 4,468,488 | 8/1984 | Minagawa et al. ......... 546/190 |

Primary Examiner—Paul R. Michl
Assistant Examiner—Alex H. Walker
Attorney, Agent, or Firm—Harry Falber

[57] ABSTRACT

Compounds of the formula I

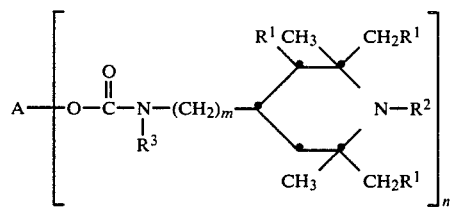

in which m is zero, 1 or 2 and n is 2, 3 or 4, $R^1$ is hydrogen or $C_1$–$C_4$-alkyl, A is the n-valent radical of a polyol and $R^2$ and $R^3$ are monovalent radicals as defined in claim 1, are outstanding light stabilizers for organic materials, particularly for organic polymers.

12 Claims, No Drawings

N-(POLYALKYLPIPERIDINYL)-CARBAMATES OF POLYOLS

The invention relates to novel derivatives of polyalkylpiperidines which are N-substituted carbamates of di-, tri- or tetra-ols, and to their use as stabilisers for polymers, particularly against damage caused to the latter by light. The invention also relates to the polymers which have been stabilised by means of these novel compounds.

German Offenlegungsschrift No. 2,040,975 describes derivatives of 4-amino-2,2,6,6-tetramethylpiperidine as light stabilisers for polymers, amongst them also the corresponding 4-alkoxycarbonylamino derivatives. The compound 4-(β-hydroxyethoxycarboxamido)-2,2,6,6-tetramethylpiperidine (Compound No. 7) is mentioned as an example of these, and its use in various polymers is described.

Similar compounds which differ essentially from the above compounds in the nature of the substitution of the piperidine nitrogen are recommended as light stabilisers in German Offenlegungsschrift, No. 2,349,962. The compound 4-(2-hydroxyethoxycarbonylamino)-1,2,2,6,6-pentamethylpiperidine (Compound No. 126) is described in that text as an example of a 4-carbamate, and its use as a stabiliser in high-density polypropylene and polyethylene is also described.

Similar compounds, for example the compound 4-ethoxycarboxamido-2,6-diethyl-2,3,6-trimethylpiperidine, are also described as light stabilisers in German Offenlegungsschrift No. 2,621,870.

All these compounds are monocarbamates containing a polyalkylpiperidine group on the carbamate nitrogen. They are excellent light stabilisers, but are not suitable for certain applications because of their relatively low molecular weight. For example, they can migrate rapidly or be washed out rapidly from thin layers of substrates.

Although polymeric or oligomeric carbamates (polyurethanes) containing polyalkylpiperidine groups, such as are described in German Offenlegungsschrift, No. 2,719,131 as subgroup 5, have a relatively high molecular weight, so that they are not lost rapidly through migration or washing out, their stabilising action in polyolefins is considerably weaker than that of the monocarbamates.

It has now been found, surprisingly, that di-, tri-and tetra-carbamates of polyols in which the carbamate nitrogen is substituted by polyalkylpiperidine groups, are outstanding light stabilisers for organic materials and, moreover, do not have the disadvantages of the monocarbamates or the polycarbamates of the state of the art.

The invention relates, therefore, to compounds of the formula I

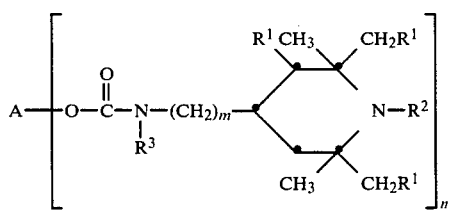

in which m is zero, 1 or 2 and n is 2, 3 or 4, $R^1$ is hydrogen or $C_1-C_4$-alkyl, $R^2$ is hydrogen, $C_1-C_{12}$-alkyl, $C_3-C_6$-alkenyl, $C_3-C_5$-alkinyl, $C_7-C_{12}$-aralkyl, glycidyl, cyanomethyl or one of the groups —CO—NH—$R^4$, —CO—N($R^5$)$_2$, —COO$R^6$, —CH$_2$COO$R^6$, —CH$_2$CON($R^5$)$_2$, —CO—$R^7$ or —CH$_2$CH($R^8$)O$R^9$, $R^3$ is hydrogen, $C_1-C_{20}$-alkyl or $C_1-C_6$-alkyl, $C_3-C_5$-alkenyl, $C_5-C_8$-cycloalkyl, $C_6-C_{12}$-cycloalkylalkyl, $C_6-C_{10}$-aryl, $C_7-C_{15}$-alkylaryl or $C_7-C_{12}$-aralkyl which is substituted by —O$R^{10}$, —OOC—$R^{11}$, —CN, —COO$R^{12}$, —N($R^{13}$)($R^{14}$) or —CON($R^{13}$)($R^{14}$), or is a group of the formula II

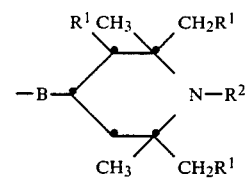

in which B is a direct bond, —CH$_2$CH$_2$— or —CH$_2$CH$_2$O—, $R^4$ is $C_1-C_8$-alkyl, $C_5-C_8$-cycloalkyl, $C_6-C_{10}$-aryl or $C_7-C_{15}$-alkylaryl, $R^5$ is $C_1-C_8$-alkyl, cycloalkyl, phenyl or benzyl, or the two radicals $R^5$, together with the N atom to which they are attached, form a 5-membered to 7-membered heterocyclic ring, $R^6$ is $C_1-C_{12}$-alkyl, $C_5-C_8$-cycloalkyl, allyl, benzyl or phenyl, $R^7$ is hydrogen, $C_1-C_{11}$-alkyl, $C_2-C_5$-alkenyl, $C_5-C_8$-cycloalkyl, phenyl or $C_7-C_{12}$-aralkyl, $R^8$ is hydrogen, methyl, ethyl, phenyl, butoxymethyl or phenoxymethyl, $R^9$ is hydrogen, $C_1-C_8$-alkyl, $C_3-C_6$-alkenyl, benzyl or —CO—$R^{11}$, $R^{10}$ is hydrogen, $C_1-C_{12}$-alkyl or $C_5-C_8$-cycloalkyl, $R^{11}$ is $C_1-C_{11}$-alkyl, $C_2-C_5$-alkenyl, $C_5-C_8$-cycloalkyl, phenyl, $C_7-C_{12}$-aralkyl or phenyl or $C_7-C_9$-phenylalkyl which is substituted by $C_1-C_4$-alkyl and/or OH, or is a group —NH—$R^4$, $R^{12}$ is $C_1-C_{12}$-alkyl, $C_5-C_8$-cycloalkyl, allyl, benzyl, $C_7-C_9$-phenylalkyl which is substituted in the phenyl radical by OH and $C_1-C_4$-alkyl, or phenyl or is a group of the formula II, $R^{13}$ is $C_1-C_8$-alkyl, cyclohexyl, benzyl, phenyl or a radical of the formula II, and $R^{14}$ is hydrogen, $C_1-C_8$-alkyl, cyclohexyl or a radical of the formula II, or $R^{14}$, together with $R^{13}$ and the N atom, forms a 5-membered to 7-membered heterocyclic radical, and A is the n-valent radical of a polyol and, if n is 2, is $C_2-C_{16}$-alkylene or is $C_4-C_{20}$-alkylene, $C_4-C_{10}$-alkenylene, $C_6-C_8$-cycloalkylene, $C_8-C_{12}$-dialkylenecycloalkane, $C_8-C_{14}$-dialkylenearene, $C_6-C_{12}$-arylene or $C_{13}-C_{18}$-diphenylenealkane which is interrupted by one or more —O— or —N($C_1-C_4$-alkyl)- groups, or is a group of the formula III

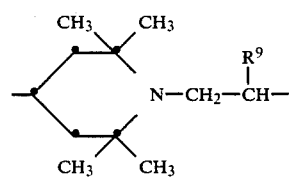

and, if n is 3, A is a trivalent aliphatic or cycloaliphatic hydrocarbon radical having 3–20 C atoms and, if n is 4, is a tetravalent aliphatic hydrocarbon radical having 4–20 C atoms, and to acid addition salts of these compounds.

In this formula $R^1$ can be a $C_1-C_4$-alkyl radical, for example methyl, ethyl, propyl, isopropyl or butyl. As $C_1-C_8$-alkyl, $R^4$, $R^5$, $R^9$, $R^{13}$ and $R^{14}$ can have the same meanings and can, additionally, also be, for example, isoamyl, n-hexyl, 2-ethylbutyl, n-heptyl, n-octyl, 2-ethylhexyl or 1,1,3,3-tetramethylbutyl. As $C_1$–$C_{11}$-alkyl, $R^7$ and $R^{11}$ can, additionally, also be, for example, isononyl, n-decyl or n-undecyl, and, as $C_1$–$C_{12}$-alkyl, $R^2$, $R^6$, $R^8$ and $R^{10}$ can, additionally, also be, for example, n-dodecyl. As $C_1$–$C_{20}$-alkyl, $R^3$ can, additionally, also be, for example, tetradecyl, hexadecyl, octadecyl or eicosyl. All the alkyl groups can be unbranched or branched.

$R^3$, $R^4$, $R^6$, $R^7$, $R^{10}$, $R^{11}$ and $R^{12}$ can be $C_5$–$C_8$-cycloalkyl, for example cyclopentyl, cyclohexyl, methylcyclohexyl, cycloheptyl or cyclooctyl. As cycloalkylalkyl, $R^3$ can, for example, be cyclopentylmethyl, cyclohexylmethyl, 2-cyclohexylethyl, 2-cyclooctylethyl or 3-cyclohexylpropyl.

As $C_3$–$C_6$-alkenyl, $R^2$, $R^3$ and $R^9$ are, in particular, ($C_2$–$C_5$-alkenyl)-alkyl, for example allyl, methallyl, 3,3-dimethylallyl or 2,3,3-trimethylallyl. As $C_3$–$C_5$-alkinyl, $R^2$ can, for example, be propargyl or 2-butinyl.

As $C_7$–$C_{12}$-aralkyl, $R^2$, $R^3$, $R^7$ and $R^{11}$ are, in particular, phenylalkyl, for example benzyl, 2-phenylethyl, 3-phenylpropyl or 1-phenylisopropyl.

As $C_6$–$C_{10}$-aryl, $R^3$ and $R^4$ can be phenyl or naphthyl. As $C_7$–$C_{15}$-alkylaryl, $R^3$ and $R^4$ are, in particular, alkylphenyl, for example tolyl, xylyl, 4-tert.-butylphenyl, 4-hexylphenyl or 4-octylphenyl.

As phenyl or $C_7$–$C_9$-phenylalkyl which is substituted by $C_1$–$C_4$-alkyl and/or OH, $R^{11}$ can, for example, be tolyl, xylyl, 4-isopropylphenyl, 2-hydroxyphenyl, 3,5-di-tert.-butyl-4-hydroxyphenyl, 4-methylbenzyl, 3-hydroxybenzyl, 3-methyl-4-hydroxy-5-tert.-butylbenzyl or 2-[3,5-di-tert.-butyl-4-hydroxyphenyl]-ethyl.

As $C_7$–$C_9$-phenylalkyl which is substituted in the phenyl radical by OH and $C_1$–$C_4$-alkyl, $R^{12}$ can, for example, be 3,5-di-tert.-butyl-4-hydroxybenzyl or 3-methyl-4-hydroxy-5-tert.-butylbenzyl.

If $R^{13}$ and $R^{14}$, or the two radicals $R^5$, together with the N atom to which they are attached, form a 5-membered to 7-membered heterocyclic ring, this can be, for example, a pyrrolidine, piperidine, morpholine or piperazine ring. A piperazine ring of this type can be substituted in the 4-position by $C_1$–$C_4$-alkyl.

As $C_2$–$C_{16}$-alkylene, the group A can be unbranched or branched alkylene, for example 1,2-ethylene, 1,2-propylene, 1,3-propylene, 1,4-butylene, 1,6-hexylene, 1,8-octylene, 2,2-dimethyl-1,3-propylene, dodecamethylene or hexadecamethylene.

As $C_4$–$C_{20}$-alkylene which is interrupted by —O— or —N($C_1$–$C_4$-alkyl)-, A can, for example, be 3-oxa-1,5-pentylene, 4-oxa-2,6-heptylene, 3,6-dioxa-1,8-octylene, 3,6,9-trioxa-1,11-undecylene, 3-methylaza-1,5-pentylene, 4-isopropylaza-2,6-heptylene or 3-butylaza-1,5-pentylene.

As cycloalkylene or dialkylenecycloalkane, A can, for example, be 1,3-cyclohexylene, 1,4-cyclohexylene, 1,4-di(methylene)-cyclohexane or dicyclohexylmethane-4,4'-diyl.

As $C_4$–$C_{10}$-alkenylene, A can, for example, be but-2-en-1,4-ylene, hex-3-en-1,6-ylene or 2-methylbut-2-en-1,4-ylene.

As $C_8$–$C_{14}$-dialkylenearene, A can, for example, be 1,3-xylylene, 1,4-xylylene, 1,4-dimethylenenaphthalene or 1,4-diethylenebenzene. As $C_6$–$C_{12}$-arylene, A can, for example, be phenylene, naphthylene or biphenylene. As $C_{13}$–$C_{18}$-diphenylenealkane, A can, for example, be di-(p-phenylene)-methane or 2,2-di-(p-phenylene)-propane.

As a trivalent hydrocarbon radical having 3–20 C atoms, A can, for example, be propane-1,2,3-triyl, 1,1,1-trimethyleneethane, 1,1,1-trimethylenepropane or 1,2,4-trimethylenecyclohexane.

As a tetravalent hydrocarbon radical having 4–20 C atoms, A can, for example, be butane-1,2,3,4-tetrayl or tetra-(methylene)-methane.

Preferred compounds of the formula I are those in which $R^1$ is hydrogen, those in which n is 2 and those in which $R^3$ is not hydrogen.

Compounds of the formula I which are also preferred are those in which m is zero and n is 2, $R^1$ is hydrogen, $R^2$ is hydrogen, $C_1$–$C_4$-alkyl, allyl, benzyl, cyanomethyl or —CO—$R^7$, and $R^3$ is hydrogen, $C_1$–$C_{12}$-alkyl, $C_2$–$C_3$-hydroxyalkyl, cyclohexyl, phenyl, benzyl, a group of the formula II, $R^{11}$—COOCH$_2$CH$_2$—, $R^{12}$—OOC—(CH$_2$)$_p$— or $R^{13}$—NH—CO—(CH$_2$)$_p$— in which p is 1 or 2, $R^7$ is $C_1$–$C_4$-alkyl or vinyl, $R^{11}$ is $C_1$–$C_4$-alkyl, —NH—($C_1$–$C_4$-alkyl), phenyl or phenyl or phenylethyl which is substituted by an OH group and two $C_1$–$C_4$-alkyl groups, $R^{12}$ is $C_1$–$C_6$-alkyl, allyl, 3,5-di-tert.-butyl-4-hydroxybenzyl or a group of the formula II, $R^{13}$ is $C_1$–$C_6$-alkyl or a group of the formula II and A is $C_2$–$C_{12}$-alkylene, $C_4$–$C_6$-monooxaalkylene, $C_4$–$C_6$-dioxaalkylene or a group of the formula III. Compounds which are particularly preferred amongst these are those in which $R^3$ is $C_1$–$C_{12}$-alkyl, $C_2$–$C_3$-hydroxyalkyl, cyclohexyl or a group of the formula II or of the formula $R^{12}$—OOC—(CH$_2$)$_p$— in which p is 1 or 2 and $R^{12}$ is $C_1$–$C_4$-alkyl or a group of the formula II, and also those in which A is $C_2$–$C_6$-alkylene or 3-oxa-1,5-pentylene.

If the compounds of the formula I are basic compounds, they can form acid addition salts with inorganic or organic acids. Examples of such acids are phosphoric acid, phenylphosphoric acid, diethylphosphoric acid, acetic acid, formic acid, toluenesulfonic acid, methanesulfonic acid, phenylphosphonic acid or diphenylphosphinic acid.

The compounds of the formulae below are examples of individual compounds of the formula I in which n is 2:

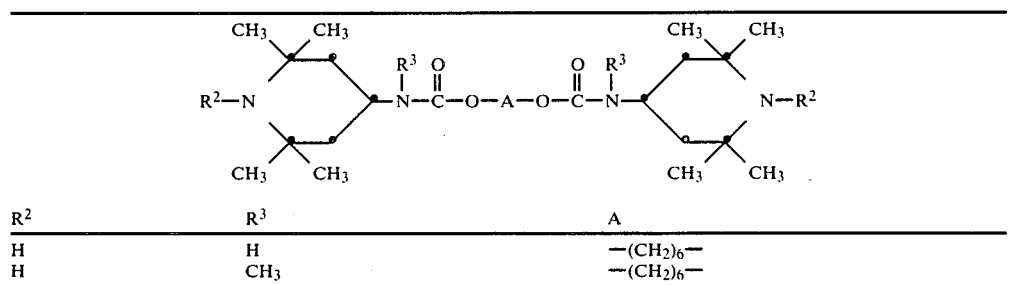

| $R^2$ | $R^3$ | A |
|---|---|---|
| H | H | —(CH$_2$)$_6$— |
| H | CH$_3$ | —(CH$_2$)$_6$— |

-continued

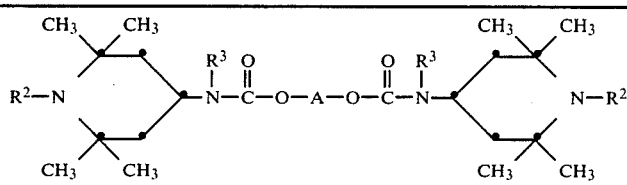

| R² | R³ | A |
|---|---|---|
| CH₃ | n-C₄H₉ | —(CH₂)₆— |
| H | n-C₄H₉ | —(CH₂)₄— |
| CH₃CO— | n-C₃H₇ | —(CH₂)₈— |
| H | n-C₈H₁₇ | —CH₂—⌬—CH₂— |
| CH₃CO— | n-C₄H₉ | —CH₂CH₂OCH₂CH₂— |
| H | n-C₄H₉ | —CH₂CH₂N(CH₃)CH₂CH₂— |
| CH₂=CHCO— | n-C₄H₉ | —CH₂CH=CHCH₂— |
| CH₃ | n-C₁₂H₂₅ | —⌬—C(CH₃)₂—⌬— |
| CH₂=CH₂CH₂— | H | —⌬—CH₂—⌬— |
| NC—CH₂— | ⌬— | —(CH₂)₄— |
| ⌬—CH₂— | ⌬—CH₂— | —(CH₂)₁₂— |
| CH₃ | —CH₂CH₂COO—piperidinyl(N—CH₃) | —(CH₂)₆— |

The compounds of the formulae below are examples of compounds of the formula I in which n is 3:

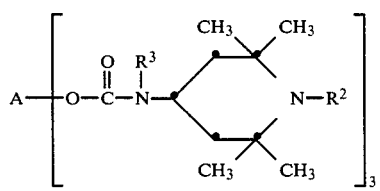

| R² | R³ | A |
|---|---|---|
| H | n-C₄H₉ | —CH₂—CH(—)—CH₂— |

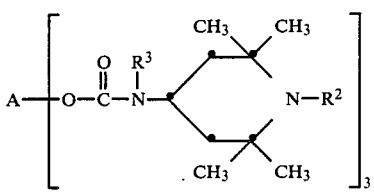

| $R^2$ | $R^3$ | A |
|---|---|---|
| H | iso-$C_8H_{17}$ | $CH_3C(CH_2-)_3$ (with $CH_2-$, $CH_2-$, $CH_2-$) |
| $CH_3$ | $-CH_2CH_2COOC_2H_5$ | $CH_3C(CH_2-)_3$ |
| $CH_3CO-$ | $CH_3$ | $C_2H_5C(CH_2-)_3$ |
| H | n-$C_4H_9$ | $C_2H_5C(CH_2-)_3$ |
| $CH_2=CHCO-$ | n-$C_4H_9$ | $-CH_2-CH-(CH_2)_3-CH_2-$ |

The compounds of the formulae below are examples of compounds of the formula I in which n is 4:

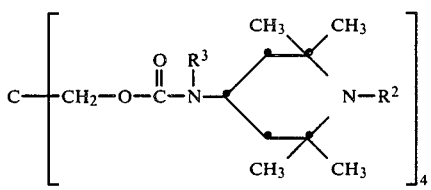

| $R^2$ | $R^3$ |
|---|---|
| H | $-CH(C_2H_5)-C_3H_7$ |
| $CH_3$ | n-$C_4H_9$ |
| $CH_3CO-$ | $-CH_2COOCH_3$ |
| H | n-$C_{12}H_{25}$ |
| $CH_3$ | $-CH_2CH_2CONH-$ (connected to piperidine with $CH_3,CH_3,CH_3,CH_3$ and $N-CH_3$) |

The compounds of the formula I can be prepared in a simple manner by reacting a di-, tri- or tetra-chlorocarbonate of a polyol IV with the corresponding 4-aminopiperidine V

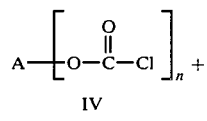

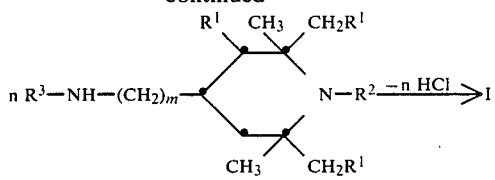

The reaction is carried out in an inert organic solvent and takes place virtually quantitatively at room temperature if the hydrogen chloride formed is neutralised by adding n equivalents of a base. The base used can be an inorganic base, for example NaOH, KOH, $NaHCO_3$, $Na_2CO_3$, $K_2CO_3$, CaO, MgO, $CaCO_3$ etc., or an organic base, such as a trialkylamine, dialkylaniline or pyridine.

It is particularly advantageous to carry out the reaction in a 2-phase system. The first phase consists of a solution of the component V in a water-immiscible solvent, for example toluene, xylene, benzene, cyclohexane, ligroin, methylene dichloride, chloroform, carbon tetrachloride, 1,2-dichloroethane, diethyl ether or diisopropyl ether. The other phase consists of a solution or suspension of the base in water. The component IV is added slowly to the 2-phase mixture with stirring, preferably as a solution in the organic solvent used. In this process the temperature should not exceed 80° C.; preferably the temperature is kept at $-10°$ to $+50°$ C., in particular 0° to $+30°$ C.

After the reaction the aqueous phase is separated off and the organic phase is evaporated, the compounds of the formula I being obtained in a high yield and a satisfactory state of purity.

If the reaction is carried out without an aqueous phase, the base and the resulting hydrochloride of the base can be soluble or insoluble in the organic solvent used. In the first case, the chloride formed is removed by washing with water, in the second case it is removed by filtration. Water-soluble solvents, for example dioxane, tetrahydrofuran, acetonitrile or dimethylformamide, are also suitable as the solvent in this case. It is also possible to use mixtures of such polar solvents with non-polar solvents. If the reaction is carried out in a single-phase system, it is advantageous to warm the reaction mixture to 60°-150° C. after adding the component V, in order to complete the reaction.

The compounds of the formula IV are known compounds and can be prepared from the corresponding polyols by reaction with phosgene. The compounds of the formula V in which p is zero are known from German Offenlegungsschriften Nos. 2,040,975, 2,349,962 and 2,621,870, which have already been mentioned. The compounds of the formula V in which p is 1 or 2 can be prepared by hydrogenating the corresponding nitriles and subseouently introducing the radical R³, as is described, for example, in German Offenlegungsschrift No. 2,352,379.

A second method of preparing the compounds of the formula I consists in reacting alkyl carbamates of the formula VI with the polyols VII:

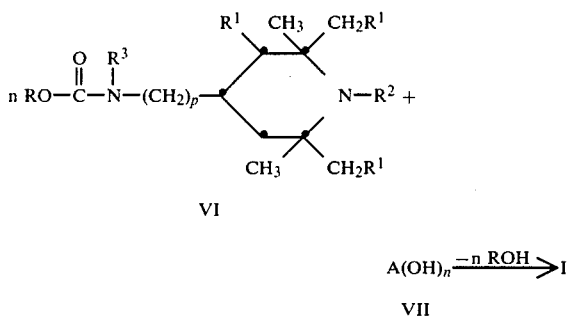

$$A(OH)_n \xrightarrow{-n\ ROH} I$$

VII

R being a $C_1$–$C_4$-alkyl radical.

This reaction is accelerated by trans-esterification catalysts, for example alkali metals, titanium alkoxides or organotin compounds. The reaction is preferably carried out without a solvent and by removing the ROH by distillation at temperatures of 120°-200° C. However, the products obtained thereby are not as pure as the products obtained by the first process, so that in general the first process is to be preferred.

As a variant of both processes, it is also possible to introduce the radical R² subsequently. In this case, therefore, a carbamate of the formula I in which R² is hydrogen is first prepared, and this hydrogen atom is replaced in a second reaction stage by one of the radicals just mentioned for R², excepting hydrogen. This can be effected by the methods generally known for the substitution of secondary amines, for example by reaction with the corresponding halogen compounds R²Hal in the presence of a base, which binds the hydrogen halide formed thereby. The methyl group can be introduced by the Eschweiler-Clark method by reaction with CH₂O/HCOOH. The cyanomethyl group can be introduced by reaction with CH₂O/HCN. Acyl groups can also be introduced by reaction with carboxylic anhydrides. The introduction of a group —CH₂CH(R⁸)OR⁹ can be effected by reaction with an oxirane

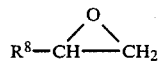

and, if appropriate, subsequent etherification or esterification of the resulting N-hydroxyalkyl compound by the methods customary for this reaction.

The compounds of the formula I can be used as stabilisers for organic polymers; they are distinguished, in particular, by an outstanding light stabilising action. The following are examples of such polymers:

1. Polymers of monoolefins and diolefins, for example polyethylene (which can be crosslinked), polypropylene, polyisobutylene, polybut-1-ene, polymethylpent-1-ene, polyisoprene or polybutadiene, and also polymers of cycloolefins, for example cyclopentene or norbornene.

2. Mixtures of the polymers mentioned under 1, for example mixtures of polypropylene with polyethylene or with polyisobutylene.

3. Copolymers of monoolefins and diolefins with one another or with other vinyl monomers, for example ethylene propylene copolymers, propylene/but-1-ene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers, and salts thereof (ionomers), and also terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, for example styrene/butadiene, styrene/acrylonitrile, styrene/ethyl methacrylate, styrene butadiene/ethyl acrylate or styrene/acrylonitrile/methyl acrylate; mixtures of high impact strength obtained from styrene copolymers and another polymer, for example a polyacrylate, a diene polymer or an ethylene/propylene/diene terpolymer; and block copolymers of styrene, for example styrene butadiene/styrene, styrene/isoprene/styrene, styrene/ethylene-butylene/styrene or styrene/ethylene-propylene/styrene.

6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under 5, for example those known as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers and especially polymers obtained from halogen-containing vinyl compounds, for example polyvinyl chloride, polyvinylidene chloride, polyvinyl fluoride and polyvinylidene fluoride; and copolymers thereof, such as vinyl chloride/vinylidene chloride, vinyl chloride/vinyl acetate or vinylidene chloride vinyl acetate.

8 Polymers derived from α,β-unsaturated acids and derivatives thereof, such as polyacrylates and polymethacrylates, polyacrylamides and polyacrylonitriles.

9. Copolymers of the monomers mentioned under 8 with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers derived from unsaturated alcohols and amines or acyl derivatives or acetals thereof, such as polyvinyl alcohol, polyvinyl acetate, stearate, benzoate or maleate, polyvinyl butyral, polyallyl phthalate and polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene, and also polyoxymethylenes containing comonomers, for example ethylene oxide.

13. Polyphenylene oxides and sulfides.

14. Polyurethanes derived on the one hand from polyesters and polybutadiene containing terminal hydroxyl groups and, on the other hand, from aliphatic or aromatic polyisocyanates, and precursors thereof (polyisocyanates, polyols or prepolymers).

15. Polyamides and copolyamides derived from diamines and dicarboxylic acids and/or aminocarboxylic acids or the corresponding lactams, such as polyamide 4, polyamide 6, polyamide 6/6, polyamide 6/10, polyamide 11, polyamide 12, poly-2,4,4-trimethylhexamethyleneterephthalamide and poly-m-phenyleneisophthalamide and copolymers thereof with polyethers, for example polyethylene glycol, polypropylene glycol or polytetramethylene glycol.

16. Polyureas, polyimides and polyamide-imides.

17. Polyesters derived from dicarboxylic acids and diols and/or hydroxycarboxylic acids or the corresponding lactones, such as polyethylene terephthalate, polybutylene terephthalate, poly-1,4-dimethylolcyclohexane terephthalate, poly[2,2-bis-(4-hydroxyphenyl)-propane]terephthalate and polyhydroxybenzoates and also block polyether-esters derived from polyethers having terminal hydroxyl groups, dialcohols and dicarboxylic acids.

18. Polycarbonates.

19. Polysulfones and polyether-sulfones.

20. Crosslinked polymers derived from aldehydes on the one hand and from phenols, urea and melamine on the other hand, such as phenol-formaldehyde, urea-formaldehyde and melamine-formaldehyde resins.

21. Drying and non-drying alkyd resins.

22. Unsaturated polyester resins derived from copolyesters of saturated and unsaturated dicarboxylic acids with polyhydric alcohols, and also vinyl compounds as crosslinking agents, and also halogen-containing modifications thereof of low combustibility.

23. Crosslinked acrylic resins derived from substituted acrylic acid esters, for example epoxyacrylates, urethaneacrylates or polyesteracrylates.

24. Alkyd resins, polyester resins and acrylic resins which have been crosslinked with melamine resins, urea resins, polyisocyanates or epoxide resins.

25. Crosslinked epoxide resins derived from polyepoxides.

26. Naturally occurring polymers, such as cellulose, natural rubber and gelatin, and also their polymer-analogously chemically modified derivatives, such as cellulose acetates, propionates and butyrates, and the cellulose ethers, such as methylcellulose.

Particular importance attaches to the stabilisation of the polyolefins listed under 1–3, the styrene polymers listed under 4–6 and the polyurethanes and polyamides listed under 14 and 15.

The stabilisers according to the invention are added to the polymers in a concentration of 0.05 to 4% by weight, calculated on the material to be stabilised. It is preferable to incorporate into the material to be stabilised 0.1 to 2% by weight of the compounds, calculated on this material.

The incorporation can be carried out before, during or after polymerisation, for example by mixing the compounds and, if desired, further additives into the melt in accordance with the methods conventional in the art, before or during shaping. In the case of lacquers, the additive is preferably incorporated in a solution of the lacquer before the latter is applied.

The stabilisers can also be added to the polymers to be stabilised in the form of a masterbatch containing, for example, a concentration of 2.5 to 25% by weight of these compounds.

In addition to the compounds of the formula I, it is also possible to add other known stabilisers to the polymers. Examples of these are afforded by the following classes of stabilisers:

1. Antioxidants 1.1. Alkylated monophenols, such as 2,6-di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert. -butyl-4-i-butylphenol, 2,6-dicyclopentyl-4-methyl-phenol, 2-(α-methylcyclohexyl)-4,6-dimethylphenol, 2,6-di-octadecyl-4-methylphenol, 2,4,6-tricyclohexylphenol and 2,6-di-tert.-butyl-4-methoxymethylphenol.

1.2. Alkylated hydroquinones, such as 2,6-di-tert.-butyl-4-methoxyphenol, 2,5-di-tert.-butyl-hydroquinone, 2,6-di-tert.-amyl-hydroquinone and 2,6-di-phenyl-4-octadecyloxyphenol.

1.3. Hydroxylated thiodiphenyl ethers, such as 2,2'-thio-bis-(6-tert.-butyl-4-methylphenol), 2,2'-thio-bis-(4-octylphenol), 4,4'-thio-bis-(6-tert.-butyl-3-methylphenol) and 4,4'-thio-bis-(6-tert.-butyl-2-methylphenol).

1.4. Alkylidene-bisphenols, such as 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-tert.-butyl-4-isobutylphenol), 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)-butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], di-(3-tert.-butyl-4-hydroxy-5-methylphenyl)-dicyclopentadiene and di-[2-(3'-tert.-butyl-2'-hydroxy-5'-methylbenzyl)-6-tert.-butyl-4-methylphenyl]terephthalate.

1.5. Benzyl compounds, such as 1,3,5-tri-(3,5-di-tert.-butyl-4-hydroxybenzyl)-2,4,6-trimethylbenzene, di-(3,5-di-tert.-butyl-4-hydroxybenzyl) sulfide, isooctyl 3,5-di-tert.-butyl-4-hydroxybenzylmercaptoacetate, bis-(4-tert.-butyl-3-hydroxy-2,6-dimethylbenzyl)-dithiol terephthalate, 1,3,5-tris-(3,5-di-tert.-butyl-4-hydroxybenzyl) isocyanurate, 1,3,5-tris-(4-tert.-butyl-3-hydroxy-2,6-dimethylbenzyl) isocyanurate, dioctadecyl 3,5-di-tert.-butyl-4-hydroxybenzylphosphonate and the calcium salt of monoethyl 3,5-di-tert.-butyl-4-hydroxybenzylphosphonate.

1.6. Acylaminophenols, such as 4-hydroxylauranilide, 4-hydroxystearanilide and 2,4-bis-octylmercapto-6-(3,5-di-tert.-butyl-4-hydroxyanilino)-s-triazine.

1.7 Esters of β-(3,5-di-tert.-butyl-4-hydroxyphenyl)-propionic acid with monohydric or polyhydric alcohols, for example methanol, octadecanol, 1,6-hexanediol, neopentylglycol, thiodiethylene glycol, diethylene glycol, triethylene glycol, pentaerythritol, trishydroxyethyl isocyanurate and di-hydroxyethyl-oxamide.

1.8. Esters of β-(5-tert.-butyl-4-hydroxy-3-methylphenyl)propionic acid with monohydric or polyhydric alcohols, for example methanol, octadecanol, 1,6-hexanediol, neopentylglycol, thiodiethylene glycol, diethylene glycol, triethylene glycol, pentaerythritol, trishydroxyethyl isocyanurate and di-hydroxyethyl-oxamide.

1.9. Amides of β-(3,5-di-tert.-butyl-4-hydroxyphenyl)propionic acid, for example N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)hydrazine.

2. UV absorbers and light stabilisers 2.1. 2-(2'-Hydroxyphenyl)-benztriazoles, for example the 5'-methyl-, 3',5'-di-tert.-butyl-, 5'-tert.-butyl-, 5'-(1,1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 4'-octoxy- and 3',5'-di-tert.-amyl derivative.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

2.3. Esters of substituted or unsubstituted benzoic acids, for example 4-tert.-butylphenyl salicylate, phenyl salicylate, octylphenyl salicylate, dibenzoylresorcinol, bis-(4-tert.-butylbenzoyl)-resorcinol, benzoylresorcinol and 2,4-di-tert.-butylphenyl 3,5-di-tert.-butyl-4-hydroxybenzoate.

2.4. Acrylates, for example ethyl or isooctyl α-cyano-β,β-diphenylacrylate, methyl 2-carbomethoxycinnamate, methyl or butyl α-cyano-.β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)-phenol], such as the 1:1 or 1:2 complex, optionally containing additional ligands, such as n-butylamine, triethanolamine or N-cyclohexyldiethanolamine, nickel dibutyldithiocarbamate, nickel salts of monoalkyl esters, such as the methyl or ethyl ester, of 4-hydroxy-3,5-di-tert.-butylbenzylphosphonic acid, nickel complexes of ketoximes, such as 2-hydroxy-4-methylphenyl undecyl ketone oxime, and nickel complexes of 1-phenyl-4-lauroyl-5-hydroxypyrazole, optionally containing additional ligands.

2.6. Oxalic acid diamides, for example 4,4'-di-octyloxyoxanilide, 2,2'-di-octyloxy-5,5'-di-tert.-butyloxanilide, 2,2'-di-dodecyloxy-5,5'-di-tert.-butyloxanilide, 2-ethoxy-2'-ethyloxanilide, N,N'-bis-(3-dimethylaminopropyl)-oxamide, 2-ethoxy-5-tert.-butyl-2'-ethyloxanilide and a mixture of the latter with 2-ethoxy-2'-ethyl-5,4'-di-tert.-butyloxanilide and mixtures of ortho-methoxy-substituted and para-methoxy-substituted oxanilides and of o-ethoxy-disubstituted and p-ethoxy-disubstituted oxanilides.

3. Metal deactivators, for example N,N'-diphenyloxamide, N-salicylal-N'-salicyloylhydrazine, N,N'-bis-salicyloylhydrazine, N,N'-bis-(3,5-di-tert.-butyl-4-hydroxyphenylpropionyl)hydrazine, 3-salicyloylamino-1,2,4-triazole and bis-benzylideneoxalic acid dihydrazide.

4. Phosphites and phosphonites, for example triphenyl phosphite, diphenyl alkyl phosphites, phenyl dialkyl phosphites, tri-(nonylphenyl) phosphite, trilauryl phosphite, trioctadecyl phosphite, distearyl pentaerythritol diphosphite, tris(2,4-di-tert.-butylphenyl) phosphite, diisodecyl pentaerythritol diphosphite, di-(2,4-di-tert.-butylphenyl)-pentaerythritol diphosphite, tristearyl sorbitol triphosphite and tetrakis-(2,4-di-tert.-butylphenyl)-4,4'-biphenylene diphosphonite.

5. Compounds which destroy peroxide, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto)-propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example Ca stearate, Zn stearate, Mg stearate, Na ricinoleate or K palmitate, antimony pyrocatecholate or tin pyrocatecholate.

8. Nucleating agents, for example 4-tert.-butylbenzoic acid, adipic acid or diphenylacetic acid.

If known stabilisers are concomitantly used, synergistic effects can occur, which is frequently the case when other light stabilisers or organic phosphites are concomitantly used. The concomitant use of antioxidants in stabilising polyolefins is of particular importance.

It is also possible to add other additives which are conventional in plastics technology, for example flame-proofing agents, antistatic agents, plasticisers, lubricants, blowing agents, pigments, fillers or reinforcing agents.

The invention also relates, therefore, to the organic polymers which have been stabilised by adding 0.05 to 4% by weight of at least one compound of the formula I, and which can, if desired, also contain other known and conventional additives. The plastics thus stabilised can be used in a very wide variety of forms, for example as films, fibres, tapes, profiles or binders for lacquers.

The preparation and use of the compounds according to the invention is described in greater detail in the examples which follow. In these examples, parts and percentages are by weight. The temperatures are quoted in degrees centigrade. The formula

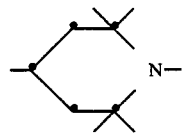

denotes a 2,2,6,6-tetramethylpiperidine radical.

EXAMPLE 1

Solutions of 50.4 g (1.26 moles) of sodium hydroxide in 200 ml of water and of 255.1 g (1.2 moles) of 4-n-butylamino-2,2,6,6-tetramethylpiperidine in 1,000 ml of toluene are combined, and cooled to approx. +5° C., in a 4-necked flask equipped with a stirrer, a thermometer and a dropping funnel. A solution of 135.6 g (0.6 mole) of 1,4-butanediol bis-chlorocarbonate in 250 ml of toluene is added dropwise to this mixture in the course of approx. 6 hours, while stirring vigorously, the internal temperature being kept at 5°-10° by slight external cooling. Stirring is then continued overnight at room temperature. The two phases are then separated. The organic phase is washed with three times 100 ml of water and dried over sodium sulfate, and the toluene is removed completely by distillation in vacuo. The bis-carbamate of the structure

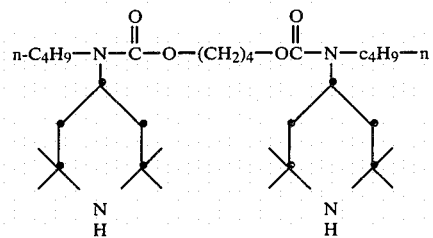

is recrystallised once in hexane and melts at 75°-76°. Its $^1$H-NMR spectrum is in agreement with the structure indicated.

| $C_{32}H_{62}N_4O_4$ | calculated: | C 67.80 | H 11.02 | N 9.88% |
|---|---|---|---|---|
| (566.87) | found: | C 67.91 | H 10.94 | N 9.93%. |

The following compounds, 1–40, are prepared analogously to Example 1 from the corresponding amines and esters of chlorocarbonic acid:

TABLE 1

| Compound No. | $R^2$ | $R^3$ | A | Melting point |
|---|---|---|---|---|
| 1 | H | $C_2H_5$ | $-(CH_2)_4-$ | 97–98° |
| 2 | H | n-$C_4H_9$ | $-(CH_2)_4-$ | 75–77° |
| 3 | H | n-$C_8H_{17}$ | $-(CH_2)_4-$ | 66–68° |
| 4 | H | (cyclohexyl) | $-(CH_2)_4-$ | 121–23° |
| 5 | Benzyl | n-$C_4H_9$ | $-(CH_2)_4-$ | 105–07° |
| 6 | H | $-CH_2CH_2OH$ | $-(CH_2)_4-$ | 153–55° |
| 7 | H | $-CH_2CH_2OOCCH_3$ | $-(CH_2)_4-$ | viscous oil |
| 8 | H | n-$C_4H_9$ | $-(CH_2)_2-$ | viscous oil |
| 9 | H | $CH_3$ | $-(CH_2)_{10}-$ | oil |
| 10 | H | $CH_3$ | $-(CH_2)_6-$ | 120–22° |
| 11 | Allyl | $CH_3$ | $-(CH_2)_6-$ | 86–87° |
| 12 | H | $C_2H_5$ | $-(CH_2)_6-$ | 78–79° |
| 13 | H | n-$C_4H_9$ | $-(CH_2)_6-$ | 95–97° |
| 14 | $CH_2=CH-CO-$ | n-$C_4H_9$ | $-(CH_2)_6-$ | oil |
| 15 | H | n-$C_8H_{17}$ | $-(CH_2)_6-$ | 85–86° |
| 16 | $CH_3CO-$ | n-$C_8H_{17}$ | $-(CH_2)_6-$ | 53–55° |
| 17 | H | n-$C_{12}H_{25}$ | $-(CH_2)_6-$ | 76–78° |
| 18 | $CH_3$ | $CH_3$ | $-(CH_2)_6-$ | 71–72° |
| 19 | H | (cyclohexyl) | $-(CH_2)_6-$ | 170–72° |
| 20 | H | $-CH_2COOH$ | $-(CH_2)_6-$ | ~230° |
| 21 | H | $-CH_2COOC_2H_5$ | $-(CH_2)_6-$ | 82–83° |
| 22 | H | $-CH_2CH_2COOC_2H_5$ | $-(CH_2)_6-$ | 96–97° |
| 23 | $CH_2=CH-CH_2-$ | $-CH_2COOCH_2CH=CH_2$ | $-(CH_2)_6-$ | viscous oil |
| 24 | H | $CH_3$ | $-CH_2CH_2OCH_2CH_2-$ | viscous oil |
| 25 | $CH_3CO-$ | $CH_3$ | $-CH_2CH_2OCH_2CH_2-$ | viscous oil |
| 26 | H | n-$C_4H_9$ | $-CH_2CH_2OCH_2CH_2-$ | viscous oil |
| 26a | H | n-$C_8H_{17}$ | $-CH_2CH_2OCH_2CH_2-$ | viscous oil |

TABLE 1-continued $$R^2-N\underset{CH_3\ CH_3}{\overset{CH_3\ CH_3}{\diamond}}\underset{R^3}{N}-\overset{O}{C}-O-A-O-\overset{O}{C}-\underset{R^3}{N}\underset{CH_3\ CH_3}{\overset{CH_3\ CH_3}{\diamond}}N-R^2$$

| Compound No. | $R^2$ | $R^3$ | A | Melting point |
|---|---|---|---|---|
| 27 | H | (2,2,6,6-tetramethylpiperidin-4-yl, NH) | $-(CH_2)_4-$ | 163–64° |
| 28 | H | (2,2,6,6-tetramethylpiperidin-4-yl, NH) | $-(CH_2)_6-$ | 153–54° |
| 29 | $CH_3$ | (2,2,6,6-tetramethylpiperidin-4-yl, N—$CH_3$) | $-(CH_2)_4-$ | 149–50° |
| 30 | H | $-CH_2COO-$(2,2,6,6-tetramethylpiperidin-4-yl, NH) | $-(CH_2)_4-$ | 156–58° |
| 31 | H | $-CH_2COO-$(2,2,6,6-tetramethylpiperidin-4-yl, NH) | $-(CH_2)_6-$ | 144–46° |
| 32 | Allyl | $-CH_2COO-$(2,2,6,6-tetramethylpiperidin-4-yl, N—Allyl) | $-(CH_2)_4-$ | oil |
| 33 | H | $-CH_2CH_2COO-$(2,2,6,6-tetramethylpiperidin-4-yl, NH) | $-(CH_2)_4-$ | 89–91° |
| 34 | H | $-CH_2CH_2COO-$(2,2,6,6-tetramethylpiperidin-4-yl, NH) | $-(CH_2)_6-$ | 114–16° |
| 35 | H | $-CH_2CH_2COO-$(2,2,6,6-tetramethylpiperidin-4-yl, N—$CH_3$) | $-(CH_2)_6-$ | 132–34° |

TABLE 1-continued

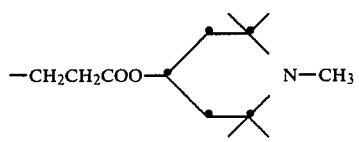

| Compound No. | R² | R³ | A | Melting point |
|---|---|---|---|---|
| 36 | CH₃ | —CH₂CH₂COO—[piperidine N—CH₃] | —(CH₂)₆— | 130–32° |
| 37 | H | —CH₂CH₂CONH—[piperidine NH] | —(CH₂)₆— | ~80° (amorphous) |
| 38 | CH₃ | —CH₂CH₂CONH—[piperidine N—CH₃] | —(CH₂)₄— | ~90° (amorphous) |
| 39 | H | n-C₄H₉ | —CH₂CH₂—N[piperidine] | 98–100° |

The compounds 40 and 41 are prepared analogously:

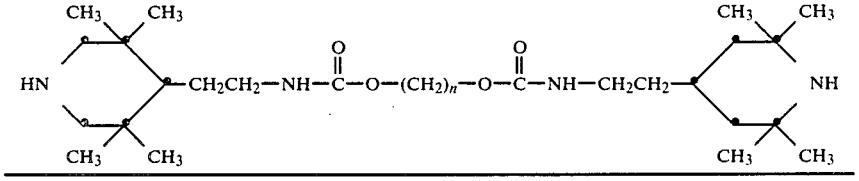

| | | |
|---|---|---|
| Compound No. 40 | n = 4 | Melting point 96–97° |
| Compound No. 41 | n = 6 | Melting point 78–79° |

EXAMPLE 2

The stabilisation of polypropylene films 100 parts of polypropylene powder (Moplen ®, fibre grade, manufactured by Montedison) are homogenised in a Brabender plastograph for 10 minutes at 200° with 0.2 part of octadecyl β-(3,5-di-tert.-butyl-4-hydroxyphenyl)-propionate, 0.1 part of calcium stearate and 0.25 part of a stabiliser from Table 1 above. The composition thus obtained is taken out of the kneader as quickly as possible and is compressed in a toggle press to give a sheet 2–3 mm thick. Part of the resulting crude moulding is cut out and compressed between two high-gloss hard aluminium foils by means of a laboratory hydraulic press for 6 minutes at 260° to give a film 0.1 mm thick, which is immediately chilled in cold water. Sections are then punched out of this film and are exposed in a Xenotest 1200. These test specimens are taken out of the exposure apparatus at regular intervals of time and their carbonyl content is tested in an IR spectrophotometer. The increase in the carbonyl extinction at 5.85 μm during the exposure is a measure of the photooxidative degradation of the polymer (see L. Balaban et al., J. Polymer Sci., Part C; 22 (1969), 1059–1071) and is, according to experience, associated with a falling off in the mechanical properties of the polymer. The time taken to reach a carbonyl extinction of approx. 0.3, at which the comparison film is brittle, is taken as a measure of the protective action.

In order to check the volatility and extractability by water, (a) one part of the samples was heated at 120° for 7 days in a circulating air oven before exposure, and (b) another part of the samples was treated for 7 days with water at 90° before exposure.

Table 2 shows the results, with and without pretreatment of the samples.

TABLE 2

| Stabilizer Compound No. | Exposure time to reach a carbonyl extinction of 0.3 (hours) | | |
|---|---|---|---|
| | without pretreatment | 7 days at 120° | 7 days extraction with water at 90° |
| — | 1100 | 290 | 310 |
| 1 | >5600 | 1320 | 690 |
| 2 | >5600 | 2920 | 2930 |
| 3 | >5750 | >5750 | 3040 |
| 4 | >4000 | >4000 | 3400 |
| 5 | >4200 | >4200 | 2500 |
| 10 | 7300 | 1250 | 485 |
| 12 | >5600 | 1170 | 780 |
| 13 | 7650 | 3900 | 4200 |
| 15 | 7670 | 6700 | 3980 |
| 17 | 6700 | 6080 | 4000 |
| 19 | >5300 | >5300 | 4150 |
| 21 | >4000 | >4000 | 650 |
| 22 | 6150 | 5670 | 490 |
| 23 | >3000 | 2280 | 1820 |
| 27 | >5240 | >5240 | 920 |
| 28 | >5120 | >5120 | 1190 |
| 29 | >4200 | >4200 | 2150 |
| 31 | >5330 | >5330 | 680 |
| 32 | >3000 | >3000 | 2900 |
| 33 | >4000 | >4000 | 810 |
| 34 | >4200 | >4200 | 770 |
| 35 | 7940 | 5100 | 1020 |
| 36 | >6100 | >6100 | 2910 |
| 37 | 7160 | 1050 | 1230 |
| 38 | >4220 | >4220 | 1090 |
| 39 | >4200 | >4200 | >4200 |
| 40 | >5300 | 2020 | 830 |
| 41 | >5100 | 1660 | 1600 |

EXAMPLE 3

Stabilising a 2-layer metal effect paint

Aluminium sheets 0.5 mm thick are coated with an aluminium-pigmented priming paint based on polyester/cellulose acetobutyrate/melamine resin. A clear lacquer of the following composition is sprayed onto the wet priming paint:

58.3 parts of Viacryl ® VC 373 (acrylic resin manufactured by Vianova, Vienna), 27.3 parts of Maprenal ® MF 590 (melamine resin manufactured by Hoechst AG, Frankfurt), 1.0 part of a 1% solution of a silicone resin in xylene, 4.0 parts of Solvesso ® 150 (mixture of aromatic solvents), 5.4 parts of xylene and 4.0 parts of ethylglycol acetate.

To this is added 0.9 part of the light stabiliser indicated in Table 3. This clear lacquer has a viscosity of 21 seconds/DIN cup 4. It is applied in a layer thickness of 40 μm and is stoved for 39 minutes at 130° C.

The samples are subjected to weathering for 4,000 hours in an UVCON accelerated weathering device manufactured by Atlas, at a cycle consisting of 4 hours UV irradiation at 60° and 4 hours weathering at 50°. The 20° gloss as specified in DIN 67,530 is determined after every 1,000 hours. In addition, the samples are examined for cracking under a stereomicroscope. The results are listed in Table 3.

TABLE 3

| Light stabiliser | 20° gloss after | | | | | Cracking noticeable after |
|---|---|---|---|---|---|---|
| | 0 hours | 1,000 hours | 2,000 hours | 3,000 hours | 4,000 hours | |
| none | 97 | 47 | 9 | — | — | 2,000 hours |
| Compound No. 16 | 95 | 71 | 41 | 23 | — | 3,000 hours |
| Compound No. 25 | 96 | 78 | 61 | 22 | 18 | 4,000 hours |

What is claimed is:

1. A compound of the formula

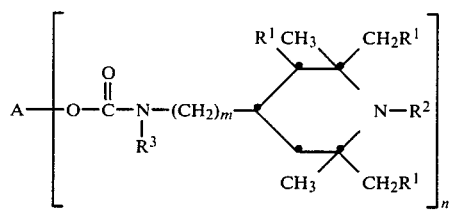

in which m is zero, 1 or 2 and n is 2, 3 or 4, $R^1$ is hydrogen or $C_1$-$C_4$-alkyl, $R^2$ is hydrogen, $C_1$-$C_{12}$-alkyl, $C_3$-$C_6$-alkenyl, $C_3$-$C_5$-alkinyl, $C_7$-$C_{12}$-aralkyl, glycidyl, cyanomethyl or one of the groups —CO—NH—$R^4$, —CO—N($R^5$)$_2$, —COO$R^6$, —CH$_2$COO$R^6$, —CH$_2$CON($R^5$)$_2$, —CO—$R^7$ or —CH$_2$CH($R^8$)O$R^9$, $R^3$ is hydrogen, $C_1$-$C_{20}$-alkyl or $C_1$-$C_6$-alkyl, $C_3$-$C_5$-alkenyl, $C_5$-$C_8$-cycloalkyl, $C_6$-$C_{12}$-cycloalkylalkyl, $C_6$-$C_{10}$-aryl, $C_7$-$C_{15}$-alkylaryl or $C_7$-$C_{12}$-aralkyl which is substituted by —O$R^{10}$, —OOC—$R^{11}$, —CN, —COO$R^{12}$, —N($R^{13}$)($R^{14}$) or —CON($R^{13}$)($R^{14}$), or is a group of the formula II

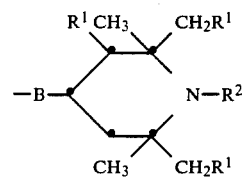

in which B is a direct bond, —CH$_2$CH$_2$— or —CH$_2$CH$_2$O—, $R^4$ is $C_1$-$C_8$-alkyl, $C_5$-$C_8$-cycloalkyl, $C_6$-$C_{10}$-aryl or $C_7$-$C_{15}$-alkylaryl, $R^5$ is $C_1$-$C_8$-alkyl, cycloalkyl, phenyl or benzyl, or the two radicals $R^5$, together with the N atom to which they are attached, form a 5-membered to 7-membered heterocyclic ring, $R^6$ is $C_1$-$C_{12}$-alkyl, $C_5$-$C_8$-cycloalkyl, allyl, benzyl or phenyl, $R^7$ is hydrogen, $C_1$-$C_{11}$-alkyl, $C_2$-$C_5$-alkenyl, $C_5$-$C_8$-cycloalkyl, phenyl or $C_7$-$C_{12}$-aralkyl, $R^8$ is hydrogen, methyl, ethyl, phenyl, butoxymethyl or phenoxymethyl, $R^9$ is hydrogen, $C_1$-$C_8$-alkyl, $C_3$-$C_6$-alkenyl, benzyl or —CO—$R^{11}$, $R^{10}$ is hydrogen, $C_1$-$C_{12}$-alkyl or $C_5$-$C_8$-cycloalkyl, $R^{11}$ is $C_1$-$C_{11}$-alkyl, $C_2$-$C_5$-alkenyl, $C_5$-$C_8$-cycloalkyl, phenyl, $C_7$-$C_{12}$-aralkyl or phenyl or $C_7$-$C_9$-phenylalkyl which is substituted by $C_1$-$C_4$-alkyl and/or OH, or is a group —NH—$R^4$, $R^{12}$ is $C_1$-$C_{12}$-alkyl, $C_5$-$C_8$-cycloalkyl, allyl, benzyl, $C_7$-$C_9$-phenylalkyl which is substituted in the phenyl radical by OH and $C_1$-$C_4$-alkyl, or phenyl or is a group of the formula II, $R^{13}$ is $C_1$-$C_8$-alkyl, cyclohexyl, benzyl, phenyl or a radical of the formula II, and $R^{14}$ is hydrogen, $C_1$-$C_8$-alkyl, cyclohexyl or a radical of the formula II, or $R^{14}$, together with $R^{13}$ and the N atom, forms a 5-membered to 7-membered heterocyclic radical, and A is the n-valent radical of a polyol and, if n is 2, is $C_2$-$C_{16}$-alkylene or is $C_4$-$C_{20}$-alkylene, $C_4$-$C_{10}$-alkenylene, $C_6$-$C_8$-cycloalkylene, $C_8$-$C_{12}$-dialkylenecycloalkane, $C_8$-$C_{14}$-dialkylenearene, $C_6$-$C_{12}$-arylene or $C_{13}$-$C_{18}$-diphenylenealkane which is interrupted by one or more —O— or —N($C_1$-$C_4$-alkyl)- groups, or is a group of the formula III

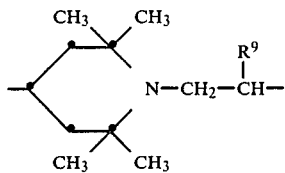

and, if n is 3, A is a trivalent aliphatic or cycloaliphatic hydrocarbon radical having 3–20 C atoms and, if n is 4, is a tetravalent aliphatic hydrocarbon radical having 4–20 C atoms, and to acid addition salts of these compounds.

2. A compound according to claim 1 of the formula I in which $R^1$ is hydrogen.

3. A compound according to claim 1 of the formula I in which n is 2.

4. A compound according to claim 1 of the formula I in which $R^3$ is not hydrogen.

5. A compound according to claim 1 of the formula I in which m is zero and n is 2, $R^1$ is hydrogen, $R^2$ is hydrogen, $C_1$-$C_4$-alkyl, allyl, benzyl, cyanomethyl or —CO—$R^7$, and $R^3$ is hydrogen, $C_1$-$C_{12}$-alkyl, $C_2$-$C_3$-hydroxyalkyl, cyclohexyl, phenyl, benzyl, a group of the formula II, $R^{11}$-COOCH$_2$CH$_2$—, $R^{12}$—OO-C—(CH$_2$)$_p$— or $R^{13}$—NH—CO—(CH$_2$)$_p$— in which p is 1 or 2, $R^7$ is $C_1$-$C_4$-alkyl or vinyl, $R^{11}$ is $C_1$-$C_4$-alkyl, —NH—($C_1$-$C_4$-alkyl), phenyl or phenyl or phenylethyl which is substituted by an OH group and two $C_1$-$C_4$-alkyl groups, $R^{12}$ is $C_1$-$C_6$-alkyl, allyl, 3,5-di-tert.-butyl-4-hydroxybenzyl or a group of the formula II, $R^{13}$ is $C_1$-$C_6$-alkyl or a group of the formula II and A is $C_2$-$C_{12}$-alkylene, $C_4$-$C_6$-monooxaalkylene, $C_4$-$C_6$-dioxaalkylene or a group of the formula III.

6. A compound according to claim 5, in which $R^3$ is $C_1$-$C_{12}$-alkyl, $C_2$-$C_3$-hydroxyalkyl, cyclohexyl or a group of the formula II or of the formula $R^{12}$—OO-C—(CH$_2$)$_p$— in which p is 1 or 2 and $R^{12}$ is $C_1$-$C_4$-alkyl or a group of the formula II.

7. A compound according to claim 5, in which A is $C_2$-$C_6$-alkylene or 3-oxa-1,5-pentylene.

8. A compound according to claim 1 of formula I in which n is 2, $R^1$ and $R^2$ are hydrogen, $R^3$ is ethyl, m is zero and A is tetramethylene.

9. A compound according to claim 1 of formula I in which n is 2, $R^1$ and $R^2$ are hydrogen, $R^3$ is methyl, m is zero and A is hexamethylene.

10. A compound according to claim 1 of the formula I in which n is 2, $R^1$ and $R^2$ are hydrogen, $R^3$ is a group of the formula

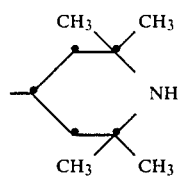

m is zero and A is hexamethylene.

11. A compound according to claim 1 of the formula I in which n is 2, $R^1$ is hydrogen, $R^2$ is methyl, $R^3$ is a group of the formula

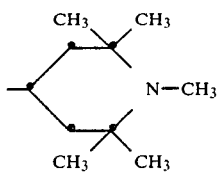

and A is tetramethylene.

12. A stabilised organic polymer containing, as the stabiliser, 0.05 to 4% by weight of at least one compound of the formula I of claim 1.

* * * * *